United States Patent [19]

Tachibana et al.

[11] Patent Number: 4,898,808

[45] Date of Patent: Feb. 6, 1990

[54] ANTISTATIC SILVER HALIDE PHOTOGRAPHIC LIGHT-SENSITIVE MATERIAL

[75] Inventors: Noriki Tachibana; Masato Nishizeki; Nobuaki Kagawa, all of Hino, Japan

[73] Assignee: Konica Corporation, Tokyo, Japan

[21] Appl. No.: 298,188

[22] Filed: Jan. 17, 1989

[30] Foreign Application Priority Data

Oct. 27, 1988 [JP] Japan ................................ 63-271672

[51] Int. Cl.[4] ........................ G03C 1/82; C08G 75/00; C07D 211/00

[52] U.S. Cl. .................................... 430/510; 430/514; 430/523; 430/527; 430/528; 430/531; 430/627; 430/630; 430/631; 430/930; 430/961; 528/391; 528/397; 528/398; 546/186; 546/191

[58] Field of Search ............... 430/510, 514, 523, 527, 430/528, 531, 627, 630, 631, 930, 961; 528/391, 397, 398; 546/186, 191

[56] References Cited

U.S. PATENT DOCUMENTS 3,988,158 10/1976 Muramatsu et al. ............... 96/87 A
4,126,467 11/1978 Miyazako et al. .................. 96/87 A

*Primary Examiner*—Hoa Yan Le
*Attorney, Agent, or Firm*—Frishauf, Holtz, Goodman & Woodward

[57] ABSTRACT

An antistatic silver halide photographic light-sensitive material having a support, provided thereon, at least one light-sensitive layer and at least one non-light-sensitive layer is disclosed. Said at least one non-light-sensitive layer comprises a polymer compound consisting essentially of a repeated structural unit represented by Formula [I], and a formamide compound represented by Formula [II];

Formula [I]

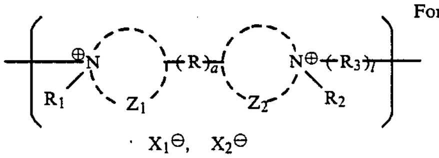

Formula [II]

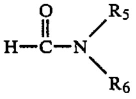

wherein $Z_1$ and $Z_2$ represent the group of the atoms necessary to form a six-membered ring with—$N^{\oplus}$—; R represents a divalent group; $R_1$ and $R_2$ represent independently one selected from the group consisting of an alkyl group and an aryl group; $R_3$ represents a hydrocarbon group; $R_5$ and $R_6$ represent independently a hydrogen atom or an alkyl group; $X_1^{\ominus}$ and $X_2^{\ominus}$ represent an anion; a and l represent an integer of 0 and 1.

76 Claims, No Drawings

ANTISTATIC SILVER HALIDE PHOTOGRAPHIC LIGHT-SENSITIVE MATERIAL

FIELD OF THE INVENTION

This invention relates to an antistatic silver halide photographic light-sensitive material and, more particularly, to an antistatic silver halide photographic light-sensitive material comprising at least one light-sensitive silver halide emulsion layer and at least one non-light-sensitive antistatic layer.

BACKGROUND OF THE INVENTION

In preparing and using a silver halide photographic light-sensitive material, there is liable to be accumulated static electricity in a light-sensitive material. Such static accumulation will cause many troubles. One of the most serious troubles is that a light-sensitive emulsion layer is hit by light emitted by discharge of static electricity prior to development of the light-sensitive material and there will resultingly produce dot-like spots or twig- or feather-like irregular and uneven density. This phenomenon is so-called a static mark that seriously impair or sometimes, entirely destroy a commercial value of a photographic light-sensitive material. Such static marks cannot be found until light-sensitive materials are developed. This trouble is, therefore, one of the very troublesome problems. The above-mentioned accumulation of static electricity also causes an adsorption of dusts on a surface of a light-sensitive material, from which other secondary troubles such as a coating trouble may be derived. Further, since the supports of any light-sensitive materials are hydrophobic, accumulation of static electricity usually becomes greater and, in addition, the higher a processing rate and a sensitivity of an emulsion, the more the static marks, so that light-sensitive materials are seriously affected thereby.

With the purpose of preventing photographic light-sensitive materials from accumulating static electricity (i.e., electrification), variety of substances have been used so far to serve as antistatic agents. They are ionic and conductive or hygroscopic substances, with which electrification may be prevented by giving a conductivity to a light-sensitive material so as to rapidly eliminate an accumulated charge in advance of discharging it.

As for the methods of providing an antistatic property directly to the supports of photographic light-sensitive materials, there have been known methods including, for example, one in which the above-mentioned substance is incorporated directly into a support comprising a macro-molecular substance, and the other in which the above-mentioned substance is coated directly over to a surface of a support. In the latter case, the surface of the support is coated with an antistatic agent directly or in mixture of such a macromolecular substance as gelatin, polyvinyl alcohol, cellulose acetate, polyvinyl formal, polyvinyl butyral and the like. There is also another method in which an antistatic agent is incorporated, as well as into a light-sensitive emulsion layer, into such a non-light-sensitive auxiliary layer as a backing layer, an antihalation layer, an interlayer, a protective layer and so forth and there is available a further method in which an antistatic agent is coated over a developed light-sensitive material so as to prevent it from adsorption of dusts in handling.

In the meantime, when using the known antistatic agents for high-speed silver halide light-sensitive materials, few of them can provide a satisfactory antistatic effect especially at the conditions of a substantially low humidity, or they lose an antistatic effect to aging. It has, therefore, been difficult to apply them. With the purpose of solving the above-mentioned troubles, there have so far been attempts to develop a variety of antistatic agents so as to apply them to photographic light-sensitive materials. For example, as described in Japanese Patent Publication Open to Public Inspection (hereinafter called Japanese Patent O.P.I. Publication) Nos. 18728/1979 and 159222/1979, the so-called ionen type polymers having a dissociative group in a main polymer chain have been applied to silver halide light-sensitive materials. However, low solubilities of those polymers in organic solvents are liable to have a defect to result in forming an opaque or striped layer on a support instead of a regular layer in applying them to a light-sensitive material, which prevents them from providing a satisfactory antistatic property.

SUMMARY OF THE INVENTION

It is an object of the invention to provide a silver halide photographic light-sensitive material having an excellent antistatic property.

Another object of the invention is to provide an antistatic agent excellent in solubility in organic solvents and in layer producibility in coating.

DETAILED DESCRIPTION OF THE INVENTION

The above-mentioned objects of the invention can be accomplished with a silver halide photographic light-sensitive material having a support, provided thereon at least one light-sensitive silver halide emulsion layer and at least one non-light-sensitive layer, wherein said at least one non-light-sensitive layer comprises an ionen type polymer compound consising essentially of a repeated structural unit represented by the following Formula [I];

Formula [I]

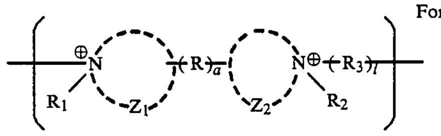

$X_1^{\ominus}$, $X_2^{\ominus}$ wherein $Z_1$ and $Z_2$ each represent the group of the atoms necessary to form a six-membered ring with—$N^{\oplus}$—; R represents a divalent group; $R_1$ and $R_2$ each represent an alkyl or aryl group; $R_3$ represents a hydrocarbon group, preferably having 1 to 20 carbon atoms; $X_1^{\ominus}$ and $X_2^{\ominus}$ each represent an anion; a and l represent independently an integer of 0 or 1.

In Formula [I], the alkyl groups represented by $R_1$ and $R_2$ preferably comprises 1 to 10 carbon atoms, and the aryl group represented thereby preferably comprises 6 to 12 carbon atoms. The alkyl group includes, more preferably, a methyl group, an ethyl group and a propyl group, in particular. The preceding groups also include those having substituents.

The divalent group represented by R includes an alkylene group.

The anions represented respectively by $X_1^{\ominus}$ and $X_2^{\ominus}$ include, for example, a halogen ion, $R_4OSO_3^{\ominus}$, $R_4SO_3^{\ominus}$ and $(HO)_2POO^{\ominus}$. $X_1^{\ominus}$ and $X_2^{\ominus}$ may be the same with or different from each other. $R_4$ represents a hydrogen atom, a substituted or non-substituted phenyl group or an alkyl group having 1 to 8 carbon atoms.

In addition to the foregoing polymer compound represented by Formula [I]; at least one non-light-sensitive layer preferably contains a formamide compound represented by the following Formula [II];

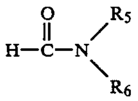

Formula [II]

wherein $R_5$ and $R_6$ represent a hydrogen atom or an alkyl group, provided that one of $R_5$ and $R_6$ is always a hydrogen atom.

The ionen type polymer compound consisting essentially of a repeated structural unit represented by Formula [I] (hereinafter called the polymer compound of the invention) is represented preferably by the following Formula [III];

Formula [III]

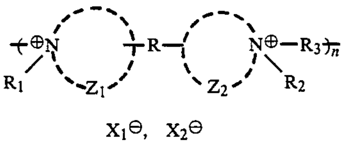

wherein $Z_1$, $Z_2$, $R_1$, $R_2$, $R_3$, R, $X_1^{\ominus}$ and $X_2^{\ominus}$ represent the same groups as those defined in Formula [I]; n represents an integer or 1 to 200, preferably 3 to 100, provided that the polymer compound of the invention is generally the mixture of the compounds having different n number, wherein n represents an average number.

Further, the polymer compound consisting essentially of a repeated structural unit represented by Formula [I] is more preferably by the following Formula [III-A];

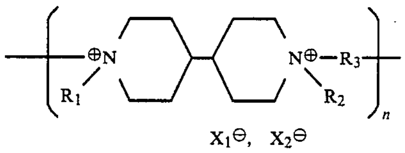

wherein $R_1$, $R_2$, $R_3$, $X_1^{\ominus}$ and $X_2^{\ominus}$ each are synonymous with those denoted in the foregoing Formula [I]; and n is an integer of 1 to 200 and, preferably 3 to 100, provided that the polymer compound of the invention is generally the mixture comprising of the polymer compounds having different n number, wherein n represents an average number.

The polymer compound represented by Formula [III] and [III-A] can be synthesized by reacting the diamine compounds represented by the following Formula [IV] or [IV-A] with the compounds represented by the following Formula [V].

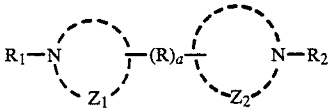

Formula [IV]

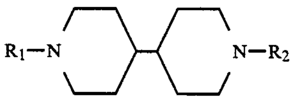

Formula [IV-A]

Formula [V]

$X_1-R_3-X_2$ wherein $Z_1$ and $Z_2$ represent an alkylene group including the substituted one; R, $R_1$, $R_2$, $R_3$, $X_1$, $X_2$ and a represent the same groups and number as those defined in Formula [I].

Some examples of the diamine compounds represented by Formula [IV] and [IV-A] are given below.

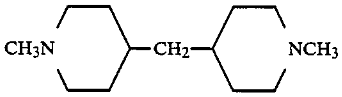

IV-1

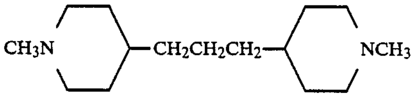

IV-2

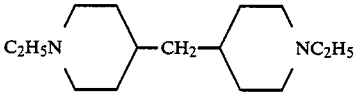

IV-3

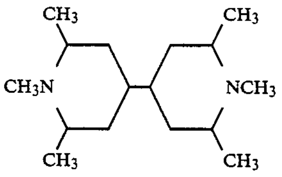

IV-4

-continued
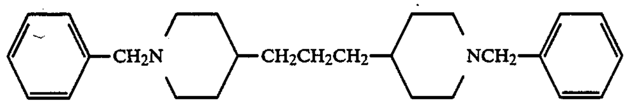
IV-5
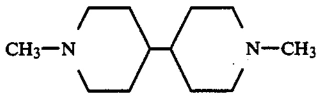
IV-6
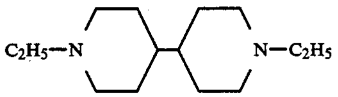
IV-7
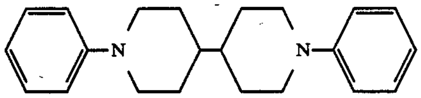
IV-8
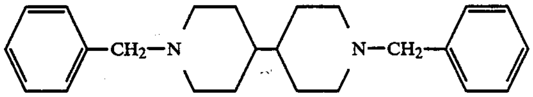
IV-9
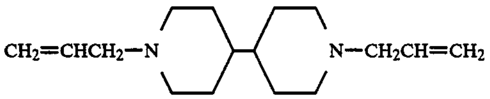
IV-10
Some examples of the compounds represented by Formula [V] are given below.
$ClCH_2CH_2Cl$ V-1
OH
|
$BrCH_2CHCH_2Br$ V-2
V-3
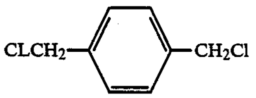
V-4
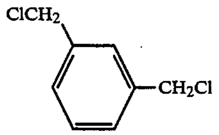
-continued
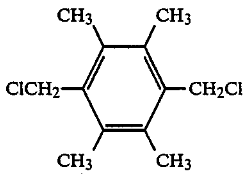
V-5
V-6
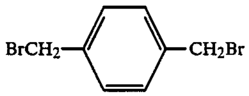
Some examples of the polymer compound of the invention represented by Formulae [III] and [III-A] are given below.
I-1
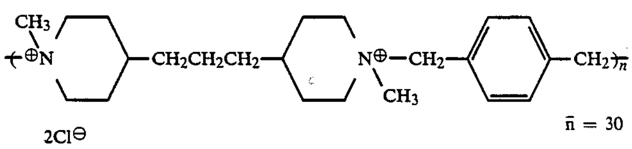
I-2
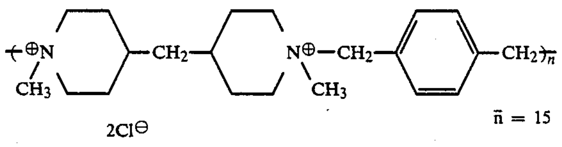

-continued
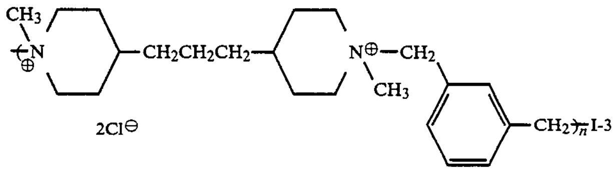
I-3
n̄ = 20
I-4
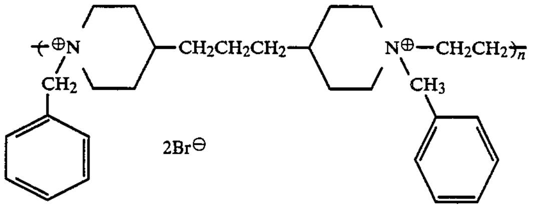
n̄ = 5
I-5
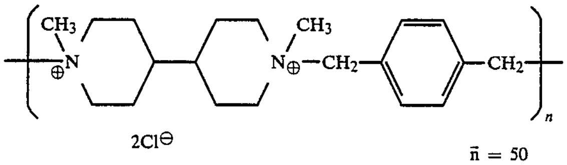
n̄ = 50
I-6
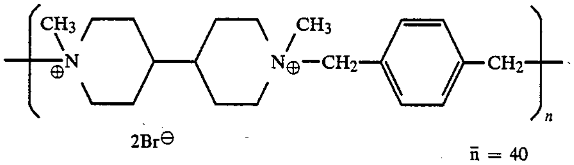
n̄ = 40
I-7
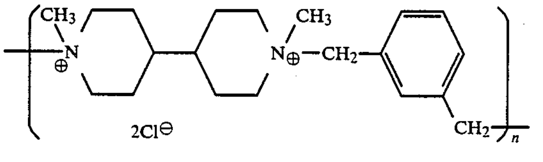
n̄ = 50
I-8
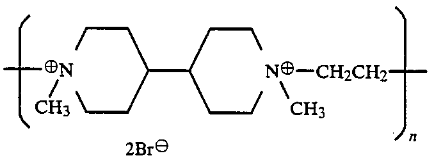
n̄ = 20
I-9
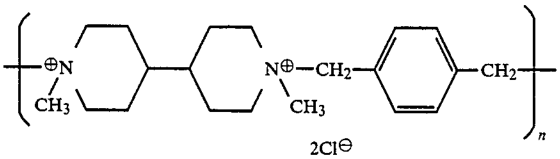
n̄ = 50
I-10
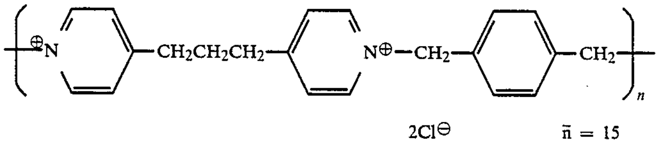
n̄ = 15
Some examples of the formamide compound of the invention are given below.
II-1 $HCONH_2$ II-2 $HCONH \cdot CH_3$ The polymer compound of the invention may be used in a suitable amount according to a variety of the kinds of photographic light-sensitive materials used, the positions to which the polymer compound is added, the coating methods and so forth. It may be used preferably in an amount of 0.01 to 1.0 g per square meter of a photographic light-sensitive material and, preferably, 0.03 to 0.4 g.

The formamide compound of the invention is incorporated into a non-sensitive layer together with the polymer compound of the invention at a constitution ratio, preferably of 100 to 1000 weight parts per 100 weight parts of the polymer compound.

The polymer and formamide compounds of the invention hereinafter called the compounds of the invention are incorporated into the non-light-sensitive layers constituting a silver halide photographic light-sensitive material. Such non-light-sensitive layers include, for example, a surface protective layer, an interlayer, a filter layer, a backing layer, a subbing layer, an overcoating layer and so forth. Particularly, the compounds of the invention are preferably incorporated into an outermost layer of a silver halide photographic light-sensitive material, such as a backing layer and an overcoating layer, a layer adjacent to an outermost backing layer and/or a layer adjacent to a subbing layer.

The polymer compound of the invention may be used independently or in combination with various macromolecular substances to form the above-mentioned non-light-sensitive layers.

The compound of the invention may be applied to such a layer as mentioned above in the following method. The compound of the invention is dissolved in water, an organic solvent such as methanol, ethanol, acetone, methylethyl ketone, ethyl acetate, acetonitrile, dioxane, dimethyl formamide, formamide, dimethylsulfoxide, methyl cellosolve, ethyl cellosolve and so forth, or the mixture thereof, and the resulted coating solution is sprayed or coated, or the light-sensitive material is dipped into the solution, and then dried.

The polymer compound of the invention may be used together with such a binder as gelatin, polyvinyl alcohol, cellulose acetate, cellulose acetate-phthalate, polyvinyl formal, polyvinyl butyral and the like, so as to form an antistatic layer.

The supports applicable to the invention include, for example, films of polyoleffin such as polyethylene, polystyrene, cellulose derivative such as cellulose triacetate, and polyester such as polyethyleneterephthalate, baryta paper, synthetic paper, paper coated on the both sides with the preceding polymers and the similar articles thereof.

The silver halide light-sensitive materials of the invention include a variety of silver halide light-sensitive materials, for example, such an ordinary black-and-white light-sensitive material as those for photographing, X-rays and graphic arts, such an ordinary multilayered color light-sensitive material as a color reversal film, a color negative film and a color positive film. The compound of the invention is particularly effective to high-speed silver halide light-sensitive materials.

The light-sensitive materials of the invention are particularly effective for use at the conditions of a humidity not higher than 20% RH.

In the light-sensitive materials of the invention, the ligh-sensitive silver halide emulsion layers exhibit those containing an silver halide emulsion substantially having a light-sensitivity, namely, a silver halide emulsion having such a satisfactory light-sensitivity as is capable of forming a photographic image. For those silver halide emulsions, it is possible to use any of ordinary types of silver halide emulsions comprising silver bromide, silver bromoiodide, silver chloroiodide, silver bromochloride, silver chloride and the like to serve as the silver halides.

The above-mentioned silver halide emulsions may be chemically sensitized by a sulfur-sensitization method, a selenium-sensitization method, a reduction-sensitization method, a noble metal-sensitization method or the like.

The above-mentioned silver halide emulsions may be spectrally sensitized to a desired wavelength region by making use of the dyes known as the spectral sensitizing dyes in the photographic art.

The silver halide photographic light-sensitive materials of the invention may also contain any of a variety of couplers, anti-color-foggants, hardeners, plasticizers, polymer latexes, UV absorbers, formalin scavengers, mordants, development accelerators, development inhibitors, fluorescent brightening agents, matting agents, lubricants, antistatic agents, surface active agents and so forth.

The silver halide photographic light-sensitive materials of the invention can be developed by the same processes as those for the conventional silver halide photographic light-sensitive materials to form an image.

EXAMPLES

The invention will be detailed with reference to the examples thereof. It is, however, to be understood that the invention shall not be limited thereto.

REFERENTIAL EXAMPLE (Antistatic Property of the polymer compound of the invention)

Fifteen (15) grams each of the polymer compounds (I-1, to I-6) of the invention and comparative compounds (A) and (B) were dissolved respectively in 20 ml of water. The resulted solutions were diluted respectively with a mixed solvent of 650 ml of methanol and 350 ml of acetone, and then coated respectively over one side of a polyethylene terephthalate film, and dried up. Each of the coated amounts was 150 mg/m$^2$. A specific surface resistance of each sample was measured to compare the antistatic properties of the samples.

Measurement of a specific surface resistance:

An insulation resistance meter: Model TR-8651 made by Takeda Riken Co., Ltd.

Electrodes: 10 cm length, 0.14 cm electrodes distance, made of brass (tip made of stainless steel), Time: one minute Conditions: 25° C. and 30% RH The results are shown in Table-1.

Comparative compounds (A)

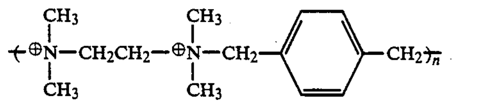

$2Cl^{\ominus}$

Viscosity * 0.12
n = 10

-continued

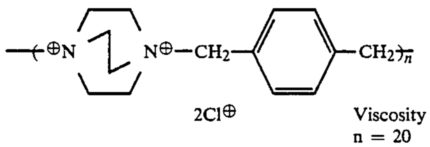

(B)

Viscosity * 0.10
n = 20

TABLE 1

| Sample No. | Antistatic Agent | Specific Surface Resistance (Ω) |
|---|---|---|
| 1 | Polymer compound of the invention, I-1 | $5.5 \times 10^9$ |
| 2 | Polymer compound of the invention, I-2 | $3.3 \times 10^9$ |
| 3 | Polymer compound of the invention, I-3 | $4.9 \times 10^9$ |
| 4 | Polymer compound of the invention, I-4 | $2.5 \times 10^9$ |
| 5 | Polymer compound of the invention, I-5 | $3.2 \times 10^9$ |
| 6 | Polymer compound of the invention, I-6 | $4.0 \times 10^9$ |
| 7 | Comparative compound (A) | $1.5 \times 10^{12}$ |
| 8 | Comparative compound (B) | $1.0 \times 10^{10}$ |

From the results shown in Table-1, it is found that the polymer compounds of the invention can remarkably lower the specific surface resistance.

The polymer compounds of the invention can dissolve well in organic solvents.

EXAMPLE 1

Each of the layers having the following composition was formed on a triacetyl cellulose film support in order from the support side to prepare a multilayered color photographic light-sensitive material Sample No. 9.

Layer 1 (an antihalation layer): a gelatin layer containing black colloidal silver and 2.2 g/m$^2$ of gelatin.

Layer 2 (an interlayer): a gelatin layer containing an emulsified dispersion of 2,5-di-tert-octyl hydroquinone and 1.2 g/m$^2$ of gelatin.

Layer 3 (a low-speed red-sensitive silver halide emulsion layer):
- a monodispersed emulsion (Em-I), AgBrI (an average grain size of 0.30 μm, AgI content of 6.0 mol %) . . . coated silver amount, 1.8 g/m$^2$;
- Sensitizing dye (I), $6 \times 10^{-5}$ mol per mol of silver;
- Sensitizing dye (II), $1.0 \times 10^{-5}$ mol per mol of silver;
- Cyan coupler (C-1), 0.06 mol per mol of silver;
- Colored cyan coupler (CC-1), 0.003 mol per mol of silver;
- DIR compound (D-1), 0.0015 mol per mol of silver;
- DIR compound (D-2), 0.002 mol per mol of silver; and
- Gelatin, 1.4 g/m$^2$;

Layer 4 (a high-speed red-sensitive silver halide emulsion layer):
- a monodisperse emulsion (Em-II), AgBrI (an average grain size of 0.5 μm, AgI content of 7.0 mol %) . . . coated silver amount, 1.3 g/m$^2$;
- Sensitizing dye (I), $3 \times 10^{-5}$ mol per mol of silver;
- Sensitizing dye (II), $1.0 \times 10^{-5}$ mol per mol of silver;
- Cyan coupler (C-1), 0.02 mol per mol of silver;
- Colored cyan coupler (CC-1) 0.0015 mol per mol of silver;
- DIR compound, D-2, in an amount of 0.001 mol per mol of silver;
- Gelatin, of 1.0 g/m$^2$;

Layer 5 (an interlayer): the same layer as Layer 2, containing gelatin of 1.0 g/m$^2$;

Layer 6 (a low-speed green-sensitive silver halide emulsion layer):
- Em-I . . . coated silver amount, 1.5 g/m$^2$;
- Sensitizing dye (III), $2.5 \times 10^{-5}$ mol per mol of silver;
- Sensitizing dye (IV), $1.2 \times 10^{-5}$ mol per mol of silver;
- Magenta coupler (M-1), 0.050 mol per mol of silver;
- Colored magenta coupler (CM-1), 0.009 mol per mol of silver;
- DIR compound (D-1), 0.0010 mol per mol of silver;
- DIR compound (D-3), 0.0030 mol per mol of silver;
- Gelatin, 2.0 g/m$^2$;

Layer 7 (a high-speed green-sensitive silver halide emulsion layer):
- Em-II . . . coated silver amount, 1.4 g/m$^2$;
- Sensitizing dye (III), $1.5 \times 10^{-5}$ mol per mol of silver;
- Sensitizing dye (IV), $1.0 \times 10^{-5}$ mol per mol of silver;
- Magenta coupler (M-1), 0.020 mol per mol of silver;
- Colored magenta coupler (CM-1), 0.002 mol per mol of silver;
- DIR compound (D-3), 0.0010 mol per mol of silver; and
- Gelatin, 1.8 g/m$^2$;

Layer 8 (a yellow filter layer): a gelatin layer containing an emulsified dispersion of yellow colloidal silver and 2,5-di-tert-octyl hydroquinone, Gelatin, 1.5 g/m$^2$;

Layer 9 (a low-speed blue-sensitive silver halide emulsion layer):
- a monodispersed emulsion (Em-III), AgBrI (an average grain size of 0.48 μm, AgI content of 6 mol %) . . . coated silver amount, 0.9 g/m$^2$;
- Sensitizing dye (V), $1.3 \times 10^{-5}$ mol per mol of silver,
- Yellow coupler (Y-1), 0.29 mol per mol of silver;
- Gelatin, 1.9 g/m$^2$;

Layer 10 (a high-speed blue-sensitive silver halide emulsion layer)
- a monodispersed emulsion (Em-IV), AgBrI (an average grain size of 0.8 μm AgI content of 15 mol %), . . . coated silver amount 0.5 g/m$^2$;
- Sensitizing dye (V), $1.0 \times 10^{-5}$ mol per mol of silver;
- Yellow coupler (Y-1), 0.08 mol per mol of silver
- DIR compound (D-2), 0.0015 mol per mol of silver;
- Gelatin, 1.6 g/m$^2$ Layer 11 (the first protective layer):
- a gelatin layer containing;
- AgBrI (an average grain size of 0.07 μm, AgI content of 1 mol %), . . . coated silver amount, 0.5 g/m$^2$;
- UV absorbers (UV-1) and (UV-2);
- Gelatin, 1.2 g/m$^2$;

Layer 12 (the second protective layer):
- a gelatin layer containing;
- $C_8F_{17}SO_3K$ (F-1), 20 mg/m$^2$;
- Polyorganosiloxane, 50 mg/m$^2$;
- Polymethyl methacrylate grains, an average grain size of 3.5 μm;
- Ethyl methacrylate-methyl methacrylate-methacrylic acid copolymer grains, an average grain size of 2.5 μm;
- Formalin scavenger, (HS-1);
- Gelatin in an amount of 1.2 g/m$^2$;

Besides the above, each layer was provided with polyethylene acrylate latex having an average particle size of 0.07 μm in a proportion of 10% by weight of gelatin gelatin hardeners H-1 and H-2, and surface active agents.

Next, the layers having the following compositions were provided onto the back side of the support in order from the support side, respectively.

Back Layer 1:

Polymer compound of the invention, I-1 . . . 150 $mg/m^2$;

Diethylene glycol . . . 10 $mg/m^2$;

Back Layer 2:

Diacetyl cellulose . . . 100 $mg/m^2$;

Stearic acid . . . 10 $mg/m^2$;

Fine silica grains, an average grain size of 0.2 μm . . . 50 $mg/m^2$

The layers of Sample No. 9 contain the following compounds;

Sensitizing dye (I): Anhydro-5,5'-dichloro-9-ethyl-3,3'-di-(3-sulfopropyl)thiacarbocyanine hydroxide, Sensitizing dye (II): Anhydro-9-ethyl-3,3'-di-(3-sulfopropyl)-4,5,4',5'-dibenzothiacarbocyanine hydroxide, Sensitizing dye (III): Anhydro-5,5'-diphenyl-9-ethyl-3,3'-di-(3-sulfopropyl)oxacarbocyanine hydroxide, Sensitizing dye (IV): Anhydro-9-ethyl-3,3'-di-(3-sulfopropyl)-5,6,5',6'-dibenzooxacarbocyanine hydroxide, and Sensitizing dye (V): Anhydro-3,3'-di-(3-sulfopropyl)-4,5-benzo-5'-methoxythiacyanine.

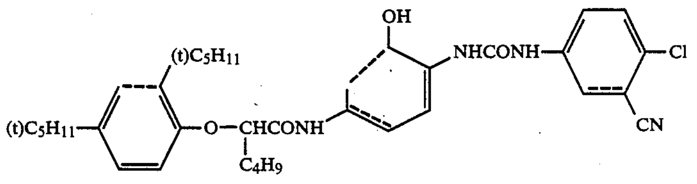

C-1

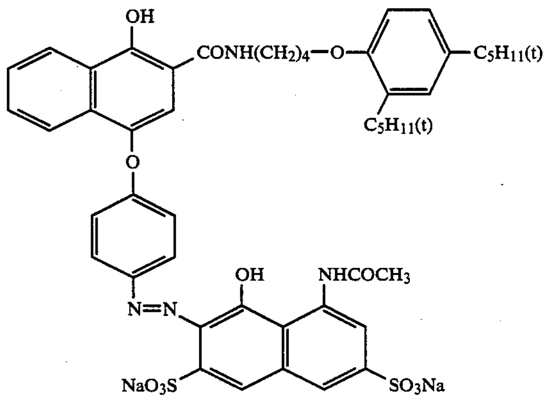

CC-1

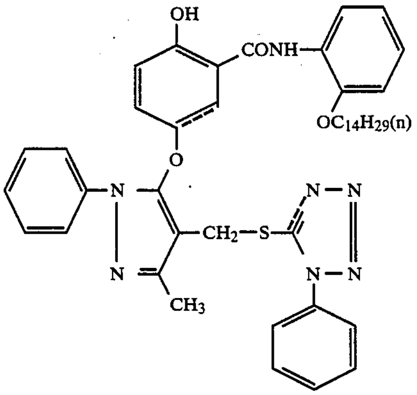

D-1

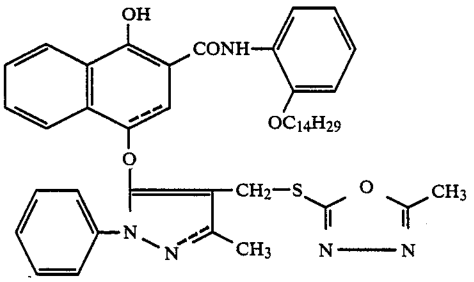

D-2

-continued
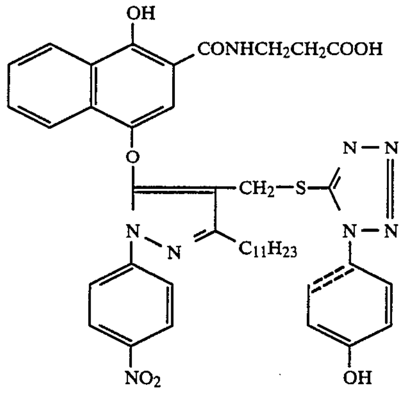
D-3
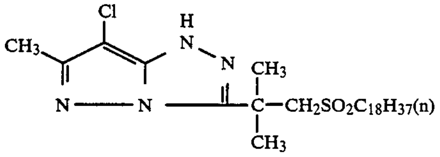
M-1
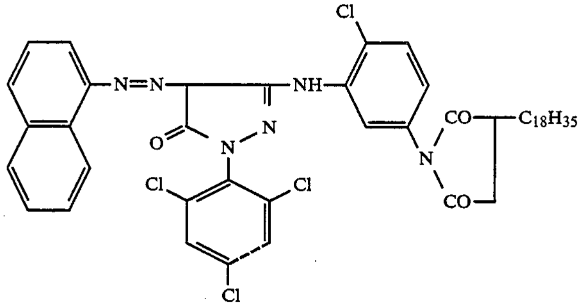
CM-1
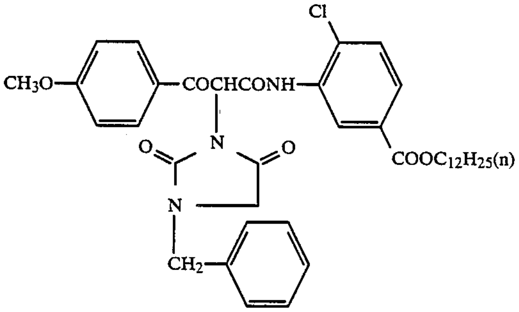
Y-1
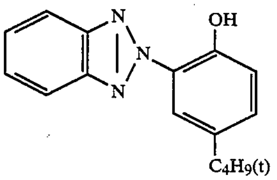
UV-1
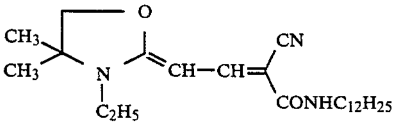
UV-2
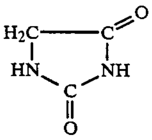
HS-1

-continued

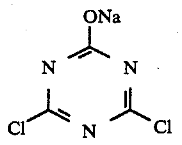

H-1

$CH_2{=}CHSO_2CH_2OCH_2SO_2CH{=}CH_2$

H-2

Sample Nos. 10 through 16 were prepared in the same manner as Sample No. 9, except that the compounds of the invention incorporated into the first back layer of Sample No. 9 were replaced as shown in Table-2.

An antistatic property of those samples were inspected by checking a static mark appearance degree and a specific surface resistance.

The static mark appearance degree was checked in the following manner; each unexposed sample was reserved at 25° C. and 25% RH for 2 hours and the emulsion-layer side of the sample was rubbed with a neoprene rubber roller in a constantly air-conditioned dark room. Then the sample was developed, bleached, fixed, washed and stabilized by the following processing solutions, and the static mark appearance degree of the sample was chacked.

The degree of the static mark appearance was evaluated by the following 4 grades.

A: No static mark is found at all,
B: A few static marks are found,
C: Considerable Static marks are found,
D: Static marks are found on the nearly whole surface of the sample.

A specific surface resistance was measured in the same manner as in the foregoing referential example.

| Processing step (38° C.) | Processing time |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |
| Drying | |

The compositions of the processing solutions used in the above-mentioned processing steps were as follows:

| | |
|---|---|
| Developing solution | |
| 4-amino-3-methyl-N—ethyl-N—(β-hydroxyethyl)aniline sulfate | 4.75 g |
| Sodium sulfite, anhydride | 4.25 g |
| Hydroxylamine ½ sulfate | 2.0 g |
| Potassium carbonate, anhydride | 37.5 g |
| Sodium bromide | 1.3 g |
| Trisodium nitrilotriacetate, monohydrate | 2.5 g |
| Potassium hydroxide | 1.0 g |
| Water added to make total quantity | 1 liter |
| Bleaching solution | |
| Ammonium ethylenediaminetetraacetate | 100.0 g |
| Diammonium ethylenediaminetetraacetate | 10.0 g |
| Ammonium bromide | 150.0 g |
| Glacial acetic acid | 10.0 ml |
| Water added to make total quantity | 1 liter |
| pH adjusted with aqueous ammonia to | 6.0 |
| Fixing solution | |

-continued

| | |
|---|---|
| Ammonium thiosulfate | 175.0 g |
| Sodium sulfite, anhydride | 8.5 g |
| Sodium metasulfite | 2.3 g |
| Water added to make total quantity | 1 liter |
| pH adjusted with acetic acid to | 6.0 |
| Stabilizing solution | |
| Formalin (37% aqueous solution) | 1.5 ml |
| Konidux manufactured by Konishiroku Photo Ind. Co., Ltd. | 7.5 ml |
| Water added to make total quantity | 1 liter |
| The results are shown in Table-2. | |

TABLE 2

| Sample No. | Antistatic agent | Specific Surface Resistance (Ω) | Degree of Static Mark |
|---|---|---|---|
| 9 | Polymer compound of the invention I-1 | $7.7 \times 10^9$ | A |
| 10 | I-2 | $6.7 \times 10^9$ | A |
| 11 | I-3 | $5.5 \times 10^9$ | A |
| 12 | I-4 | $4.3 \times 10^9$ | A |
| 13 | I-5 | $5.1 \times 10^9$ | A |
| 14 | I-6 | $5.3 \times 10^9$ | A |
| 15 | Comparative compound (A) | $3.3 \times 10^{13}$ | C |
| 16 | Comparative compound (B) | $5.3 \times 10^{10}$ | B |

From the results shown in Table-2, it is found that, in the samples of the invention, the specific surface resistances are lower and any static marks are not found at all, and that they provide excellent antistatic properties.

It is also found that in preparing the samples of the invention, they provide an excellent layer forming property in coating to form uniform coated layers.

EXAMPLE 2

With respect to Samples No. 12 through No. 16 in Example 1 and Sample No. 17 incorporating a comparative compound (C), a specific surface resistance was measured in the same manner as in the forefoing Referential Example at the conditions of 25° C. and 10% RH. The results are shown in Table 3.

TABLE 3

| Sample No. | Antistatic Agent | Specific Surface Resistance (Ω) |
|---|---|---|
| 12 | Polymer compound of the invention I-4 | $1.0 \times 10^{10}$ |
| 13 | Polymer compound of the invention I-5 | $2.5 \times 10^{10}$ |
| 14 | Polymer compound of the invention I-6 | $3.7 \times 10^{10}$ |
| 15 | Comparative compound (A) | $4.0 \times 10^{14}$ |
| 16 | Comparative compound (B) | $9.5 \times 10^{10}$ |
| 17 | Comparative compound (C) | $7.5 \times 10^{10}$ |

Comparative compound (C)

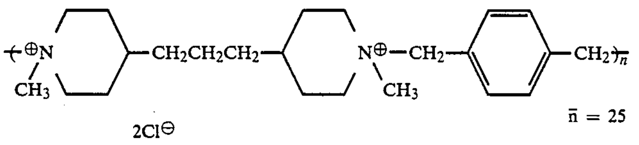

From the results shown in Table 3, it is found that, in the samples of the invention, the specific surface resistance is lower and the antistatic property is also excellent even at the condition of as low humidity as 10% RH.

EXAMPLE 3

A coating solution (1) of the following composition was coated and dried on one side of a cellulose triacetate film to a coated amount of 20 ml/$m^2$, and a coating solution (2) of the following composition was coated thereon and dried to a coated amount of 20 ml/$m^2$ to prepare Sample No. 18 having total thickness of 125 μm.

Coating solution (1)

| | Weight parts |
|---|---|
| Polymer compound of the invention (I-9) | 0.8 |
| Formamide compound of the invention (II-1) | 3 |
| Methanol | 57 |
| Acetone | 40 |
| Coating solution (2) | |
| Cellulose diacetate | 1 |
| Acetone | 50 |
| Ethyl acetate | 50 |

Sample No. 19 was prepared in the same manner as Sample No. 18, besides that the formamide compound (II-1) was replaced with ethylene glycol. Likewise, Samples No. 20 to 23 were prepared by replacing the formamide compound with the compounds as shown in Table 4.

A specific surface resistance and a haze value of each sample were measured by the following methods to compare an antistatic property and a transparency of a coated film.

Specific surface resistance: was measured in the same manner as in Referential Example.

Haze value: Six piled sample pieces (2.5 cm×2.5 cm) were put into a film holder and a transparency was measured by a turbidimeter manufactured by Tokyo Denshoku Co., Ltd.

The results are summarized in Table-4.

TABLE 4

| Sample No. | Polymer compound | Formamide compound | Specific surface resistance | Haze value (%) |
|---|---|---|---|---|
| 10 (Invention) | I-9 | Formamide (I-1) | $7 \times 10^9$ | 3.5 |
| 11 (Comparison) | I-9 | Ethylene glycol | $7 \times 10^9$ | 7.0 |
| 12 (Comparison) | I-9 | Methanol | $1.5 \times 10^{10}$ | 11.5 |
| 13 (Comparison) | I-9 | Ethyl lactate | $2.5 \times 10^{10}$ | 8.5 |
| 14 (Comparison) | I-9 | N,N—dimethylformamide | $2 \times 10^{10}$ | 9.0 |
| 15 (Comparison) | I-9 | Diethylene glycol | $7 \times 10^9$ | 6.0 |

Next, the monodispersed AgBrI emulsion containing AgI of 15 mol % was coated on the another side of the support in each of Sample Nos. 7 to 12 to a coated silver amount of 1.5 g/$m^2$ to prepare the samples of a silver halide photographic light-sensitive material. Each unexposed sample was reserved at 25° C. and 25% RH for two hours and an emulsion layer side was rubbed with a neoprene rubber roller in a consantly air-conditioned dark room. Then, the sample was processed by the conventional processing solutions used for a negative light-sensitive material. Appearance of a static mark was inspected to find that no static marks had been observed on the surface of the samples of the invention.

The followings can be found from the preceding results in the samples of the invention;

the specific surface resistances of the samples of the invention are lower than those of the comparative samples, the static marks are never found on the samples of the invention, film formation is excellent in coating an antistatic layer, and therefore, a coated film is excellent in transparency and strength.

EFFECTS OF THE INVENTION

As described in detail, the present invention can provide the silver halide photographic light-sensitive material comprising an excellent antistatic layer with a superior antistatic property as well as good film transparency and strength.

What is claimed is:

1. An antistatic silver halide photographic light-sensitive material having a support, provided thereon, at least one light-sensitive layer and at least one non-light-sensitive layer, wherein said at least one non-light-sensitive layer comprises a polymer compound consisting essentially of a repeated structural unit represented by Formula [I];

Formula [I]

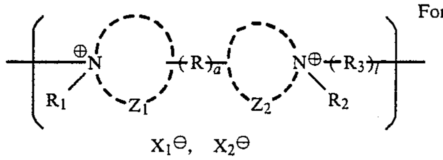

wherein $Z_1$ and $Z_2$ represent the group of the atoms necessary to form a six-membered ring with —N⊕—; R represents a divalent group; $R_1$ and $R_2$ represent independently one selected from the group consisting of an alkyl group and an aryl group; $R_3$ represents a hydrocarbon group; $X_1^{\ominus}$ and $X_2^{\ominus}$ represent an anion; a and l represent an integer of 0 and 1.

2. The material of claim 1, wherein the divalent group represented by R is an alkylene group.

3. The material of claim 1, wherein the alkyl group represented by $R_1$ and $R_2$ comprises independently 1 to 10 carbon atoms.

4. The material of claim 3, wherein the alkyl group is a methyl, ethyl or propyl group.

5. The material of claim 1, wherein the aryl group represented by $R_1$ and $R_2$ comprises independently 6 to 12 carbon atoms.

6. The material of claim 1, wherein the hydrocarbon group represented by $R_3$ comprises 1 to 20 carbon atoms.

7. The material of claim 1, wherein the anion represented by $X_1^{\ominus}$ and $X_2^{\ominus}$ is a halogen ion, $R_4OSO_3^-$, $R_4SO_3^-$ or $(HO)_2POO^-$.

8. The material of claim 7, wherein $R_4$ represents a hydrogen atom, a substituted or non-substituted phenyl group, or an alkyl group having 1 to 8 carbon atoms.

9. The material of claim 1, wherein the polymer compound consisting essentially of a repeated structural unit represented by Formula [I] is the polymer compound represented by Formula [III];

Formula [III]

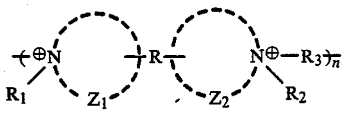

$X_1^{\ominus}$, $X_2^{\ominus}$ wherein R, $R_1$, $R_2$, $R_3$, $X_1^{\ominus}$ and $X_2^{\ominus}$ represent the same groups as those defined in Formula [I]; n represents an integer of 1 to 200.

10. The material of claim 9, wherein the divalent group represented by R is an alkylene group.

11. The material of claim 9, wherein the alkyl group represented by $R_1$ and $R_2$ comprises independently 1 to 10 carbon atoms.

12. The material of claim 11, wherein the alkyl group is a methyl, ethyl or propyl group.

13. The material of claim 9, wherein the aryl group represented by $R_1$ and $R_2$ comprises independently 6 to 12 carbon atoms.

14. The material of claim 9, wherein the hydrocarbon group represented by $R_3$ comprises 1 to 20 carbon atoms.

15. The material of claim 9, wherein the anion represented by $X_1^{\ominus}$ and $X_2^{\ominus}$ is a halogen ion, $R_4OSO_3^-$, $R_4SO_3^-$ or $(HO)_2POO^-$.

16. The material of claim 15, wherein $R_4$ represents a hydrogen atom, a substituted or non-substituted phenyl group or an alkyl group having 1 to 8 carbon atoms.

17. The material of claim 9, wherein n is an integer of 3 to 100.

18. The material of claim 9, wherein the compound represented by Formula [III] is the mixture comprising of the compounds having different n number.

19. The material of claim 18, wvhererin n represents an average number.

20. The material of claim 1, wherein the polymer compound consisting essentially of a repeated structural unit represented by Formula [I] is the polymer compound represented by Formula [III-A];

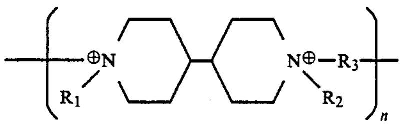

$X_1^{\ominus}$, $X_2^{\ominus}$ wherein $R_1$, $R_2$, $R_3$, $X_1^{\ominus}$ and $X_2^{\ominus}$ represent the same groups as those defined in Formula [I]; n represents an integer of 1 to 200.

21. The material of claim 20, wherein the divalent group represented by R is an alkylene group.

22. The material of claim 20, wherein the alkyl group represented by $R_1$ and $R_2$ comprises independently 1 to 10 carbon atoms.

23. The material of claim 22, wherein the alkyl group is a methyl, ethyl or propyl group.

24. The material of claim 20, wherein the aryl group represented by $R_1$ and $R_2$ comprises independently 6 to 12 carbon atoms.

25. The material of claim 20, wherein the hydrocarbon group represented by $R_3$ comprises 1 to 20 carbon atoms.

26. The material of claim 20, wherein the anion represented by $X_1^{\ominus}$ and $X_2^{\ominus}$ is a halogen ion, $R_4OSO_3^-$, $R_4SO_3^-$ or $(HO)_2POO^-$.

27. The material of claim 26, wherein $R_4$ represents a hydrogen atom, a substituted or non-substituted phenyl group or an alkyl group having 1 to 8 carbon atoms.

28. The material of claim 20, wherein n is an integer of 3 to 100.

29. The material of claim 20, wherein the compound represented by Formula [III-A] is the mixture comprising of the compounds having different n number.

30. The material of claim 29, whererin n represents an average number.

31. The material of claim 20, wherein said at least one non-light-sensitive layer comprising said polymer compound is a surface protective layer, an interlayer, a filter layer, a backing layer, a subbing layer or an overcoat layer.

32. The material of claim 31, wherein the non-light sensitive layer is a backing layer or an overcoat layer.

33. The material of claim 31, wherein said at least one non-light-sensitive layer is formed by said polymer compound in combination with other polymer substances.

34. The material of claim 33, wherein said at least one non-light-sensitive layer is formed singly by said polymer compound.

35. The material of claim 31, wherein an amount of said polymer compound added to the non-light-sensitive layer is 0.01 to 1.0 g per $m^2$ of the silver halide photographic light-sensitive material.

36. The material of claim 35, wherein the amount is 0.03 to 0.4 g per $m^2$ of the light-sensitive material.

37. The material of claim 20, wherein said polymer compound represented by Formula [III-A] is formed by reaction of the compounds represented by Formulae [IV-A] and [V-A];

Formula [IV-A]

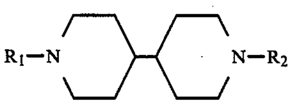

-continued $X_1—R_3—X_2$ Formula [V-A]

wherein $R_1$, $R_2$, $R_3$, $X_1$ and $X_2$ represent the same groups as those defined in Formula [I].

38. The material of claim 1, wherein the polymer compound consisting essentially of a repeated structural unit represented by Formula [I] is the polymer compound represented by Formula [III];

Formula [III]

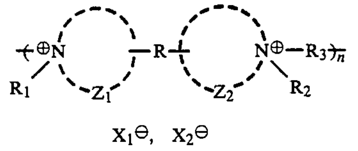

wherein R, $R_1$, $R_2$, $R_3$, $X_1^{\ominus}$ and $X_2^{\ominus}$ represent the same groups as those defined in Formula [I]; n represents an integer of 1 to 200.

39. The material of claim 38, wherein the divalent group represented by R is an alkylene group.

40. The material of claim 38, wherein the alkyl group represented by $R_1$ and $R_2$ comprises independently 1 to 10 carbon atoms.

41. The material of claim 40, wherein the alkyl group is a methyl, ethyl or propyl group.

42. The material of claim 38, wherein the aryl group represented by $R_1$ and $R_2$ comprises independently 6 to 12 carbon atoms.

43. The material of claim 38, wherein the hydrocarbon group represented by $R_3$ comprises 1 to 20 carbon atoms.

44. The material of claim 38, wherein the anion represented by $X_1^{\ominus}$ and $X_2^{\ominus}$ is a halogen ion, $R_4OSO_3^-$, $R_4SO_3^-$ or $(HO)_2POO^-$.

45. The material of claim 49, wherein $R_4$ represents a hydrogen atom, a substituted or non-substituted phenyl group or an alkyl group having 1 to 8 carbon atoms.

46. The material of claim 38, wherein n is an integer of 3 to 100.

47. The material of claim 38, wherein the compound represented by Formula [III] is the mixture comprising of the compounds having different n number.

48. The material of claim 47, wherein n represents an average number.

49. An antistatic silver halide photographic light-sensitive material having a support, provided thereon, at least one light-sensitive layer and at least one non-light-sensitive layer, wherein said at least one non-light-sensitive layer comprises a polymer compound consisting essentially of a repeated structural unit represented by Formula [I], and a formamide compound represented by Formula [II];

Formula [I]

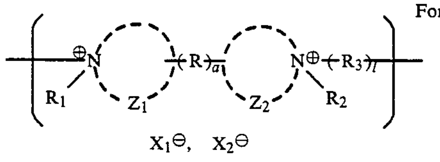

Formula [II]

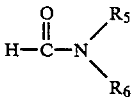

wherein $Z_1$ and $Z_2$ represent the group of the atoms necessary to form a six-membered ring with $—N^{\oplus}—$; R represents a divalent group; $R_1$ and $R_2$ represent independently one selected from the group consisting of an alkyl group and an aryl group; $R_3$ represents a hydrocarbon group; $R_5$ and $R_6$ represent independently a hydrogen atom or an alkyl group; $X_1^{\ominus}$ and $X_2^{\ominus}$ represent an anion; a and l represent an integer of 0 and 1.

50. The material of claim 49, wherein the divalent group represented by R is an alkylene group.

51. The material of claim 49, wherein the alkyl group represented by $R_1$ and $R_2$ comprises independently 1 to 10 carbon atoms.

52. The material of claim 51, wherein the alkyl group is a methyl, ethyl or propyl group.

53. The material of claim 49, wherein the aryl group represented by $R_1$ and $R_2$ comprises independently 6 to 12 carbon atoms.

54. The material of claim 49, wherein the hydrocarbon group represented by $R_3$ comprises 1 to 20 carbon atoms.

55. The material of claim 49, wherein the anion represented by $X_1^{\ominus}$ and $X_2^{\ominus}$ is a halogen ion, $R_4OSO_3^-$, $R_4SO_3^-$ or $(HO)_2POO^-$.

56. The material of claim 55, wherein $R_4$ represents a hydrogen atom, a substituted or non-substituted phenyl group, or an alkyl group having 1 to 8 carbon atoms.

57. The material of claim 49, wherein one of $R_5$ and $R_6$ is always a hydrogen atom.

58. The material of claim 49, wherein the polymer compound consisting essentially of a repeated structural unit represented by Formula [I] is the polymer compound represented by Formula [III-A];

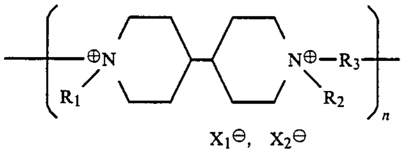

wherein $R_1$, $R_2$, $R_3$, $X_1^{\ominus}$ and $X_2^{\ominus}$ represent the same groups as those defined in Formula [I]; n represents an integer of 1 to 200.

59. The material of claim 58, wherein the divalent group represented by R is an alkylene group.

60. The material of claim 58, wherein the alkyl group represented by $R_1$ and $R_2$ comprises independently 1 to 10 carbon atoms.

61. The material of claim 60, wherein the alkyl group is a methyl, ethyl or propyl group.

62. The material of claim 58, wherein the aryl group represented by $R_1$ and $R_2$ comprises independently 6 to 12 carbon atoms.

63. The material of claim 58, wherein the hydrocarbon group represented by $R_3$ comprises 1 to 20 carbon atoms.

64. The material of claim 58, wherein the anion represented by $X_1^{\ominus}$ and $X_2^{\ominus}$ is a halogen ion, $R_4OSO_3^-$, $R_4SO_3^-$ or $(HO)_2POO^-$.

65. The material of claim 64, wherein $R_4$ represents a hydrogen atom, a substituted or non-substituted phenyl group or an alkyl group having 1 to 8 carbon atoms.

66. The material of claim 58, wherein n is an integer of 3 to 100.

67. The material of claim 58, wherein the compound represented by Formula [III-A] is the mixture comprising of the compounds having different n number.

68. The material of claim 67, whererin n represents an average number.

69. The material of claim 58, wherein said at least one non-light-sensitive layer comprising said polymer compound is a surface protective layer, an interlayer, a filter layer, a backing layer, a subbing layer or an overcoat layer.

70. The material of claim 69, wherein the non-light-sensitive layer is a backing layer or an overcoat layer.

71. The material of claim 69, wherein said at least one non-light-sensitive layer is formed by said polymer compound in combination with other polymer substances.

72. The material of claim 71, wherein said at least one non-light-sensitive layer is formed singly by said polymer compound.

73. The material of claim 69, wherein an amount of said polymer compound added to the non-light-sensitive layer is 0.01 to 1.0 g per $m^2$ of the silver halide photographic light-sensitive material.

74. The material of claim 73, wherein the amount is 0.03 to 0.4 g per $m^2$ of the light-sensitive material.

75. The material of claim 49, wherein an addition ratio of said formamide compound is 100 to 1000 weight parts per 100 weight parts of said polymer compound.

76. The material of claim 58, wherein said polymer compound represented by Formula [III-A] is formed by reaction of the compounds represented by Formulae [IV-A] and [V-A];

Formula [IV-A]

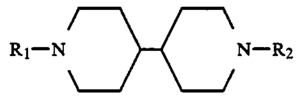

$X_1-R_3-X_2$ Formula [V-A]

wherein $R_1$, $R_2$, $R_3$, $X_1$ and $X_2$ represent the same groups as those defined in Formula [I].

* * * * *

UNITED STATES PATENT AND TRADEMARK OFFICE

CERTIFICATE OF CORRECTION

PATENT NO. : 4,898,808

DATED : February 6, 1990

INVENTOR(S) : TACHIBANA et al

It is certified that error appears in the above-identified patent and that said Letters Patent is hereby corrected as shown below:

Title page, under Section [53], insert the following:

FOREIGN PATENT DOCUMENTS -

2,544,841 8/1976 Germany
2,926,832 1/1980 Germany
2,803,025 7/1978 Germany

OTHER DOCUMENTS -

CHEMICAL ABSTRACTS, Vol.98, No.20, 16th May 1983, Abstract No.162714m, Columbus, Ohio, U.S.; & SU-A-990 786 (KIEV POLYTECHNIC INSTITUTE: UKRANIAN SCIENTIFIC-INDUSTRIAL ENTERPRISES OF THE CELLULOSE-PAPER INDUSTRY) 23-01-1983.

Column 23, claim 45, line 38, change "of claim 49" to --of claim 44--.

Signed and Sealed this

Eighth Day of December, 1992

*Attest:*

DOUGLAS B. COMER

*Attesting Officer*

*Acting Commissioner of Patents and Trademarks*